United States Patent [19]

Schamber et al.

[11] 4,288,692

[45] Sep. 8, 1981

[54] BEAM CURRENT NORMALIZATION IN AN X-RAY MICROANALYSIS INSTRUMENT

[75] Inventors: Frederick H. Schamber; Jon J. McCarthy, both of Middleton, Wis.

[73] Assignee: Tracor Northern, Inc., Middleton, Wis.

[21] Appl. No.: 63,734

[22] Filed: Aug. 6, 1979

[51] Int. Cl.³ .............................................. G01N 23/00
[52] U.S. Cl. ................................... 250/310; 250/397; 250/399
[58] Field of Search ........... 250/310, 311, 309, 396 K, 250/397, 399

[56] References Cited

U.S. PATENT DOCUMENTS 3,909,612  9/1975  Gibbard ............................ 250/310

OTHER PUBLICATIONS

"+AI Acquisition with Integrator", Schamber, 1976.
"Instrumentation", Rucklidge, *Mineralogical Ass. of Canada Short Course in Microbe Tech.*, Edmonton, Canada, May 1976.
"Artifacts Observed in Energy-Dispersive X-ray Spect. in the SEM", Fiori et al., *National Bureau of Standards Publication*, 1978.
"Electron Beam Microanalysis", Beaman et al., *ASTM Special Tech. Pub.* 506.

*Primary Examiner*—Bruce C. Anderson
*Attorney, Agent, or Firm*—Arnold, White & Durkee

[57] ABSTRACT

X-ray spectral data are normalized to beam current by basing data accumulations upon a fixed beam current integral rather than a fixed acquisition time. A current proportional to beam current is obtained from an aperture in an electron column instrument to provide a continuous monitor of beam current during data accumulation. The current is applied to a digital current integrator producing output pulses at a frequency proportional to the current. Connected to the digital current integrator is a one-shot producing a pulse of fixed width for each integrator pulse. The interval between one-shot pulses is defined as "delay time," and a signal representative of that time interval is produced and utilized to control the actual analysis time such that a prescribed beam current integral is obtained. The delay time signal may be combined with the normal system dead time signal to derive an effective dead time signal for controlling the length of actual analysis time to correct for variations in beam current as well as system dead time.

15 Claims, 11 Drawing Figures

BEAM CURRENT NORMALIZATION IN AN X-RAY MICROANALYSIS INSTRUMENT

BACKGROUND OF THE INVENTION

The present invention relates to energy dispersive spectrometry (EDS); and more particularly, the present invention relates to the stabilization of electron beam current in an electron beam column instrument for x-ray microanalysis.

The fundamental basis for EDS analysis is found in the theory of atomic structure. The structure of matter consists of chemical units, called molecules which are composed of atoms held together by chemical bonds. An atom consists of protons and neutrons in a nucleus, and electrons in orbit around the nucleus. Atoms of the various elements differ in the number of protons and neutrons in the nucleus, and also in the number of electrons.

The electrons of an atom occupy orbits, or "shells," of discrete radii essentially concentric with the nucleus. These shells constitute a number of principal quantum paths, with electrons in orbits of larger radius having higher energy levels. There may be from one to seven shells, depending upon the particular element. The shells are usually designated by number (i.e. 1 to 7), starting with the innermost shell, which number is called the principal quantum number n. The shells are also labelled with a letter notation as follows: K (n=1), L (n=2), M (n=3), N (n=4), O (n=5), P (n=6), and Q (n=7). The laws of physics limit the number of electrons in each shell to $2n^2$. Thus, there may be two electrons in the K shell, eight in the L shell, eighteen in the M shell, and thirty-two in N shell.

Each shell of an atom is further characterized by a definite minimum energy required to overcome the attraction of an electron to the nucleus and remove the electron from its shell. This minimum energy valve is referred to as the "binding energy" of an electron. Electrons closest to the nucleus require the highest binding energy and are hardest to remove, and electrons in the outermost shell of an atom require the least binding are the easiest to remove.

When an atom is bombarded by electrons having energies of only a few electron volts, the outer, more weakly bound electrons of the atom can make a transition to an unfilled shell and a higher energy state, while the more tightly bound electrons in the inner closed shells remain in their initial states. The outer electron cannot remain in the higher energy state and makes a transition back to its original ground state. Because the difference in energies is very small between the two energy states, only low energy electromagnetic radiation (photons) emission in the optical spectrum is produced.

If the electrons have sufficient energy to remove an inner electron of an atom, a vacancy is created in an inner shell. Once an inner electron has been removed, an electron from some higher energy shell can transfer to the vacant electron site. Attendant such electron transition, there is an emission of high energy electromagnetic radiation (photons), which have an energy equivalent to the energy difference between the shells of the electron transition.

Creation of a vacant electron site within an inner shell of an atom of an element, by imparting sufficient energy to the atom to overcome the binding energy of the electron occupying the site, followed by the immediate transition of an electron from one of the higher energy shells and photon emission, will, statistically, over a large number of such events, yield a characteristic emission spectrum. The emission energy lines of the spectrum will encompass intrinsic energy intensity (i.e. photons/unit time/unit area) ratios reflecting the probabilities for particular electron transitions associated with the particular inner shell vacancy. The spectrum of photon energies produced is referred to as the "characteristic x-ray spectrum."

The electromagnetic radiation spectrum, often scaled in units of frequency, can be scaled from the point of view of quantum theory in units of energy per photon. On an energy spectrum, x-rays photons have an energy $E=hv$, where h is Planck's constant and v is the frequency of radiation. Typically, x-ray photons will have energies of thousands of electron volts.

By reason of the linear relationship between the square root of the x-ray line frequency (v) and atomic number and the relationship of x-ray energies to the frequency of x-ray emission lines ($E=hv$), chemical analysis through the examination of the x-ray spectrum generated by electron bombardment can be accomplished. Such analysis is referred to as x-ray energy-dispersive analysis (EDS).

The manner of producing the characteristic x-ray spectrum for elemental analysis can be that of a primary source of electromagnetic radiation (x-ray tubes, x-rays and gamma rays from radioactive materials) or that of a charged particle beam (electrons, protons, alpha particles). The latter manner of producing characteristic x-rays can be further divided into two distinct categories, one being electron beam excitation and the other being charged particle beams produced by radioactive sources or particle accelerators.

Of primary interest relative to the present invention is the category of electron beam excitation, which is typically carried out with a so-called electron column instrument, such as a scanning electron microscope (SEM), electron microprobe (EMP), or transmission electron microscope (TEM). These electron column instruments, while being x-ray energy spectroscopy (XES) systems, are also referred to as microanalysis systems because of their capability of yielding information on a point-by-point specimen analysis basis rather than on a bulk specimen analysis basis.

In performing chemical analysis using a microanalysis system, the process sometimes being referred to as electron probe analysis (EPA), a beam of high energy (2 to 50 kev) electrons in an evacuated column is focused to a diameter of 0.1–1.0 microns at the surface of a specimen, and may also be scanned across the surface of the specimen. Upon impact with the specimen, the energetic electrons create vacancies in the inner shells of the atoms of the specimen and produce characteristic x-ray generation which is detected and the intensity quantized.

A diagram of a representative EDS analyzer for electron probe analysis is shown in FIG. 1. An electron optical system, generally indicated by the reference numeral 10, focuses a beam of electrons 12 onto a specimen 14. Optical system 10 includes an electron gun 16, magnetic condenser lens 18, objective apertures $A_1$ and $A_2$, and magnetic objective lens 20. Characteristic x-rays 22 emitted from specimen 14 impinge upon a detector 24, which is typically a lithium drifted silicon [Si(Li)] detector. An electric potential or bias is applied across detector 24. The absorption of the x-rays creates a free charge in detector 24 proportional to the energy of the x-rays, which is swept out by the bias as a charge pulse appearing at detector terminal 26.

The charge pulse on detector terminal 26 is converted to a voltage pulse by the signal processing circuitry, generally indicated by reference numeral 30, for presentation to multichannel analyzer (MCA) 32. The charge pulse is applied to a preamplifier 34 having a charge sensitive stage for integrating the total charge of the pulse and converting it to a voltage signal. Typically, the preamplifier comprises a cooled field effect transistor (FET) in close proximity to the detector. The output from the preamplifier is split into two signal paths.

One signal path is to an amplifier 36 having a high signal-to-noise ratio and long time constants, resulting in a "slow" signal throughput. In amplifier 36, a combination of differentiation and integration circuits shape the voltage pulse output from preamplifier 34 and sets the pulse width. The period of time during which the voltage output of amplifier 36 is above a threshold valve due to an input pulse, and during which time the amplifier is unable to accept pulses, is referred to as "amplifier dead time." The time constant of the pulse shaping circuitry to yield a desired output pulse width is referred to as the "shaping time constant."

Although a wide output pulse width is desirable to achieve enhanced resolution, wide pulses have an undesirable effect on pulse count rate due to "pulse pileup." The term "pulse pileup" refers to an overlapping of pulses in amplifier 36 when the time period between sequential arrivals of x-ray photons at the detector becomes less than the time required by the amplifier to process an input voltage pulse. Pulse pileup has the effects of creating through summation artificial large pulse amplitudes equivalent to detection of a higher energy photon and of creating a continuum in the region of the energy spectrum above the proper energy location, which reduces the ability to make accurate element analysis in the energy region. Because photons can arrive in any random fashion, input voltage pulses may overlap in any proportion. Thus, the effects of pulse pileup will be variously manifested during an analysis. In either case, however, pulse pileup effects may be referred to as "distortion."

The problem of pulse pileup distortion is overcome by the inclusion in signal processing circuitry 30 of a second pulse processing channel. The other of the two split signal paths from preamplifier 34 is applied to amplifier 38 which functions to process voltage pulses from preamplifier 34 much faster than does amplifier 36. The pulses output by amplifier 38 are applied to discriminator 40 for separation of real pulses from the spectrum of noise passed by amplifier 38. The separation is made based upon a preselected threshold level. The output of discriminator 40 is a normalized rectangular pulse of approximately the same duration as the output pulse from amplifier 38.

The time separation of discriminator output pulses is examined by pileup inspector circuitry 42. If the separation between discriminator pulses indicates that the pulse output from amplifier 36 due to the first input pulse from preamplifier 34 has passed its peak before the second input pulse arrived, the pileup inspector 42 signals pulse rejector 44, in series with amplifier 36, to pass the first amplifier 36 output pulse but reject the second. If the time separation indicates that the second input pulse arrived before the amplifier 36 output pulse had reached its peak, then both pulses are rejected. If, of course, the time separation between preamplifier output pulses is such that no overlap occurs, both pulses are passed by pulse rejector 44. The output pulses from pileup rejector 44 are passed to the multichannel analyzer (MCA) for sorting.

Thus, whereas the first signal processing channel with amplifier 36 functions to process input pulses to yield a high resolution energy spectrum, the second signal processing channel with amplifier 38 and discriminator 40 functions to ascertain the occurrence of input pulses too close in time to be discretely processed by amplifier 36.

MCA 32 performs a sorting function on the basis of pulse amplitude and can be referred to as a pulse height analyzer (PHA). MCA 32 registers the number of pulses that fall within discrete "increments" of pulse height within a range of pulse heights to analyze the x-ray energy spectrum. Typically, the MCA will include an analog-to-digital converter (ADC), and necessarily, a certain amount of time is required in making the conversion. This implies the existence of "dead time" in that the MCA cannot accept pulses for processing.

In view of the existence of dead time for both amplifier 36 and MCA 32, a new term "system dead time" can be defined to denote both "amplifier dead time" and "MCA dead time."

Because quantitative information of an element present in a specimen is contained in the count rate of its characteristic x-ray energy lines over a fixed time, system dead time violates the concept. Thus, there develops the necessity of correcting for dead time. The solution adopted in most EDS systems is that of establishing an "analysis time" corresponding to system "live time," that is, the actual time spent by the system in collecting data. "Analysis time" is distinguished from "acquisition time" which denotes the total time (live time plus dead time) required to complete data collection.

A fixed analysis time is established in the EDS system of FIG. 1 by a live time clock derived from a real time clock gated by clock gate 46. The gate inhibit input to clock gate 46 is generated by dead time control 48, receiving as inputs amplifier busy (AMP BUSY) and MCA bush (MCA BUSY) signals. Dead time control 48 is functionally an OR logic circuit. When amplifier 36 is occupied processing a pulse and is unavailable, AMP BUSY assumes a "high" condition and clock gate 46 inhibits passage of real time clock pulses as live time clock. Similarly, when MCA 32 is doing a conversion, MCA BUSY assumes a "high" condition and passage of real time clock pulses is inhibited.

When x-ray energy intensities are recorded over a fixed analysis time, it is assumed that the electron flux on the specimen, or beam current, which produces the x-rays remains uniform throughout that time. However, the electron beam current is subject to drift, and if the beam current changes during the analysis time, an erroneous count of energies is obtained. Previous approaches to obviating the problem of electron beam current drift have involved the utilization of apparatus for stabilizing the beam current and the application of appropriate corrections to the acquired x-ray spectral data.

Stabilization of electron beam current has been attempted using an aperture $A_2$ (see FIG. 1) which stops an annular section of the electron flux passing through the condenser lens 18 and provides a current sample proportional to the total electron flux. The aperture current sample provides a means of monitoring beam current stability and can be used as an input signal for a beam current control feedback circuit that regulates the electron gun or as an input to a beam current monitor output device for beam normalization.

Also, the aperture current sample can be converted to a train of pulses and applied as the time basis for elapsed time counting of analysis time. In such case, the aperture current controls analysis time counting instead of a real time clock.

A Faraday cup can also be used to obtain a precise measurement of the electron beam current. The Faraday cup is a closed container having a small hole through which the focused electron beam enters and on which a charge is developed. The charge on the cup is integrated to yield a current equal to beam current, which can be applied to a meter. The need to collect the entire electron beam in the cup for accurate measurement precludes beam monitoring while the specimen is actually being analyzed and requires that specimen analysis be interrupted to measure beam current.

It is also known to compensate for beam current instability by applying an aperture current sample to a current to frequency converter, the output of which is input to an updating scaler count device. The scaler counts achieved, which are related to beam current level, can be stored along with the acquired spectral data. A computer can then be used to normalize the spectral data based on the associated scaler counts. Also, the scaler counts can be read into a computer and a correction factor computer to normalize data as it is being collected.

SUMMARY OF THE INVENTION

In accordance with this invention, compensation for instability in the electron beam current of an electron beam column instrument for use in x-ray microanalysis is provided by making x-ray intensity count accumulations over a defined beam current integral (i.e. current X time). X-ray intensity count accumulation over a defined beam current integral is obtained by introducing delay time, as a function of beam current stability, in the elapsed time counting of an analysis time period to control the actual time of analysis. "Delay time" refers to a cessation in elapsed time counting of a data acquisition time period.

Delay time is introduced in the elapsed time counting of an analysis time period in an amount that will result in an actual analysis time which yields a defined beam current integral. If beam current remains stable at a preset level, delay time is introduced in a preselected amount during the counting of the analysis time period to yield an actual analysis time that provides the desired beam current integral. If, however, the beam current varies from the preset level, delay time is introduced in an amount that will change actual analysis time in inverse proportion to the change in beam current, such that the same beam current integral is obtained. That is, if beam current increases above the preset current level, delay time is reduced to shorten actual analysis time; and if beam current decreases below the preset level, delay time is increased to lengthen actual analysis time.

Compensation for electron beam current instability in accordance with the present invention may be provided in an electron beam column instrument for quantitative energy dispersive x-ray microanalysis having an optical system for establishing a focused electron beam of a preset beam current level directed onto an analysis specimen, an x-ray spectrum analyzer for accumulating a count of intensities of x-rays emitted from the specimen, and an elapsed time counter advanced by a clock of a prescribed frequency for timing out an analysis time period, by providing structure to monitor electron beam current stability and means for introducing delay time in the elapsed time counting of the analysis time period as a function of the electron beam current stability to control the time of actual x-ray intensity count accumulation, such that x-ray spectral data is acquired over a defined beam current integral.

Desirably, delay time is introduced in intervals of time of a duration that is a function of beam current. That is, delay time is introduced in intervals of constant duration so long as beam current remains stable at the preset beam current level, but is introduced in intervals that differ in duration from the constant duration if there is a variation of the beam current from the preset beam current level.

Delay time can be introduced in the elapsed time counting of an analysis time period by inhibiting operation of the elapsed time counter during the delay time intervals. Operation of the counter can be inhibited, for example, by blocking the application of clock pulses to the counter, or by disabling the counter itself. In either case, an inhibiting signal representative of delay time is desirably employed to effect an inhibiting of counter operation.

To develop a "delay time" signal for inhibiting operation of the elapsed time counter, and provided beam current normalization in an electron beam column instrument in accordance with the invention, means for producing a current proportional to beam current is connected to a digital current integrator which produces pulses, each pulse representing the integration of a defined amount of charge, and the time interval between pulses being inversely proportional to the current input. A one-shot may be connected to the output of the digital current integrator to produce a pulse of prescribed duration in response to each pulse from the digital current integrator. The one-shot output pulse is applied to logic for producing a signal in the interval between the occurrence of one-shot pulses, which signal is compatible with the means being used to inhibit the elapsed time counter. It is a signal representing the time interval between the fixed duration one-shot pulses that will be referred to as the "Delay Time signal."

The digital current integrator may desirably be a current-to-frequency converter. Accordingly, as beam current varies, the frequency of pulse production from the digital current integrator will vary in proportion thereto; and one-shot pulses of the prescribed duration will be produced at a rate proportional to beam current variation, with the Delay Time signal produced between the one-shot pulses being varied in duration in inverse proportion to beam current variation. Thus, for an increase in beam current, the duration of the Delay Time signal, which inhibits the elapsed time counter, is reduced, and the length of analysis time is reduced. And, conversely, as beam current decreases, the Delay Time signal increases in duration, thereby lengthening the analysis time.

In another aspect of the present invention, beam current normalization in an electron column instrument for x-ray microanalysis by the accumulation of x-ray spectral data over a defined beam current integral is provided in a "dead time corrected" instrument, wherein the time spent by the instrument in collecting data is controlled to account for the "dead time" of the signal processing circuitry and pulse height analyzer. In accordance with this aspect of the invention, a beam current related signal is combined with the normal dead time signal to control the length of analysis time.

In many instances, control of analysis time is achieved in dead time corrected column instruments by controlling a clock that governs the counting of an analysis time period. Typically, clock control is by means for gating the clock through to an elapsed time counter in response to a dead time signal. Accordingly, by producing a delay time signal adapted to control the clock that governs analysis time period counting, and combining the signal with the dead time signal, a composite clock control signal can be derived that adjusts the actual time of data accumulation to account for dead time and beam current instability. Using such clock control on a preset count time basis, an unambiguous and reproducible measurement in terms of actual analysis time and beam current integral is preserved.

BRIEF DESCRIPTION OF DRAWINGS

A more complete appreciation of the invention may be had by reference to the accompanying drawings, wherein.

DETAILED DESCRIPTION OF THE INVENTION

Figure 2:
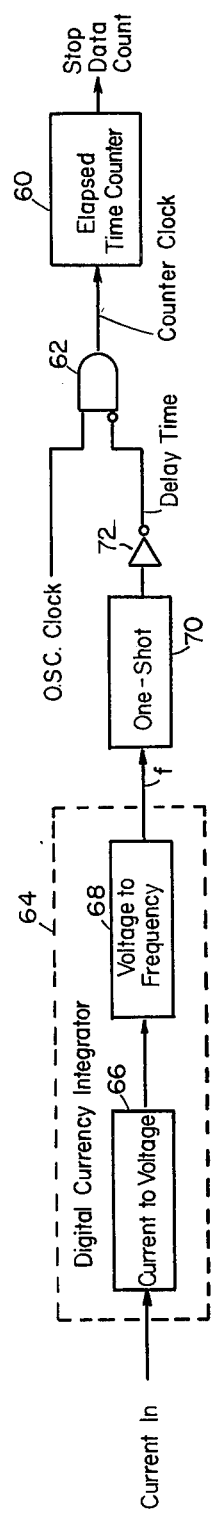
FIG. 2 is a generalized block diagram representation of one form of implementation of beam current normalization in accordance with the present invention.

Referring to FIG. 2, there is presented a block diagram representation of apparatus for providing beam current normalization in an electron column instrument for x-ray microanalysis. Beam current normalization in accordance with the present invention is achieved by basing data accumulations on a fixed beam current integral, rather than a fixed acquisition time, through adjustment of the actual time spent by the instrument in collecting data, as a function of beam current stability. The integration of beam current is an accumulation of charge over time, i.e. the product of current and time. In order for a data accumulation to be made for a constant beam current integral, that is normalized, even though the electron beam current is unstable and fluctuates during data accumulation, the time of analysis must be varied in inverse proportion to the variation in beam current. That is, if beam current increases, analysis time must be decreased in inverse proportion thereto; and if beam current decreases, analysis time must be increased in inverse proportion thereto.

An adjustment of analysis time is desirably accomplished by introducing delay time in the elapsed time counting of the analysis time period as a function of the electron beam current stability to control the length of actual analysis time. The apparatus shown in FIG. 2 functions to achieve beam current normalization through the maintenance of a fixed beam current integral by so adjusting the length of analysis time.

The counting of an analysis time period can be made using an elapsed time counter 60, which counts in steps up to a prescribed number, the counter advancing in response to clock pulses input thereto. Clock pulses for advancing elapsed time counter 60 in FIG. 2 are derived from a stable oscillator or multivibrator circuit. Oscillator clock pulses are gated through gate 62 as Counter Clock pulses to elapsed time counter 60 when the Delay Time signal is "low."

The Delay Time signal is generated by circuitry comprising a digital current integrator 64 receiving as an input thereto a current proportional to beam current. The current input may be a sample of the electron flux received on a aperture in the optical section of the electron column instrument. The digital current integrator 64 may be implemented by a current-to-frequency converter which further comprises a current-to-voltage converter 66 and a voltage-to-frequency converter 68. The output of digital current integrator 64 is applied as an input to a one-shot 70, the output of which is inverted by inverter 72 and applied as an input to gate 62 as the delay time signal.

Data accumulation continues within an analysis time period until counter 60 reaches a prescribed count, at which time, a stop data count signal is issued therefrom. Assuming a stable beam current, a known amount of delay time, and an oscillator clock of a prescribed frequency, elapsed time counter 60 can be preset to issue the stop data count signal after a prescribed time period. To further illustrate, the various signals generated in the apparatus of FIG. 2 are depicted in the timing diagram of FIG. 3.

Figure 3:
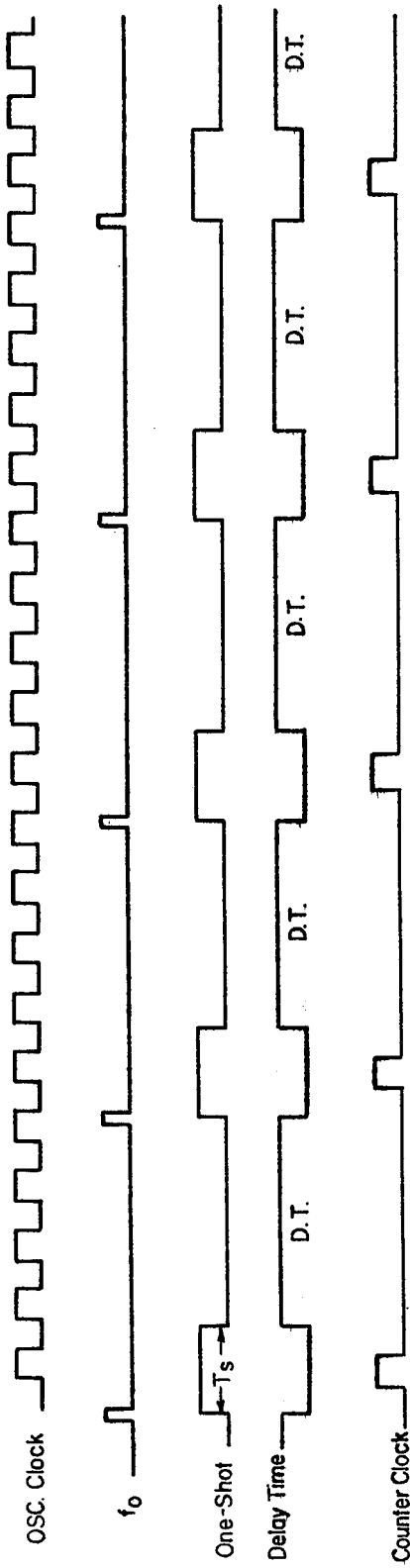
FIGS. 3, 4 and 5 are timing diagrams illustrating beam current normalization in accordance with the present invention and operation of the structure diagrammed in FIG. 2.

In FIG. 3, the oscillator clock is shown as a train of periodically occurring pulses. The output of digital current integrator 64 is a series of narrow pulses, each of which represents the integration of a certain amount of charge. If electron beam current remains stable, Current In remains stable and the output of digital current integrator 64 is a series of uniformly spaced pulses as shown. At the occurrence of the trailing edge of each digital current integrator output pulse, one-shot 70 produces a pulse of a prescribed duration $T_s$. Inverter 72 produces the Delay Time signal, a pulse that is "high" during the time interval between consecutive one-shot pulses. Again, if beam current is stable, such that digital current integrator 64 issues pulses with a uniform spacing, that uniform spacing will be maintained between one-shot pulses and delay time will be introduced in a preselected amount. The Delay Time signal from inverter 72 will enable gate 62 to pass oscillator clock pulses at a uniform rate, providing a constant rate of counting of counter 60 to the prescribed count.

Figure 4:
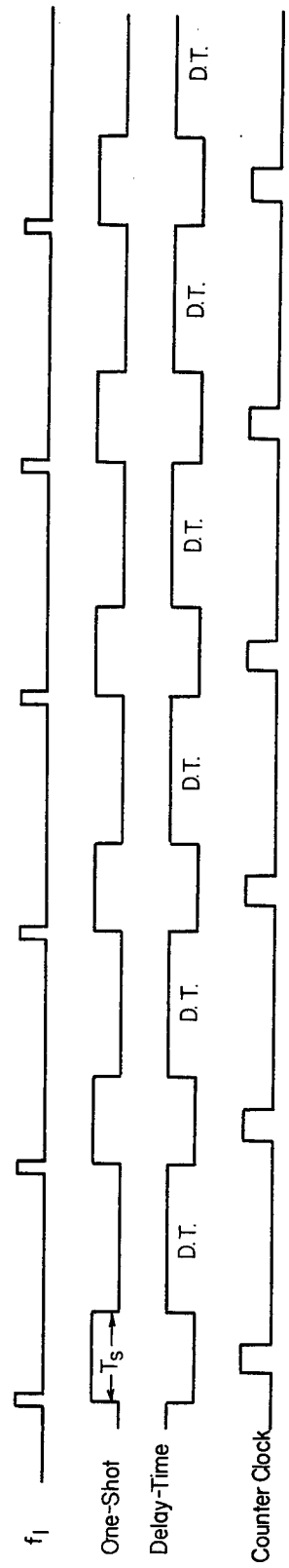

The timing diagram of FIG. 4 illustrates the effect of an increase in beam current, which results in an increase in Current In to digital current integrator 64. As shown in the diagram, the frequency of digital current integrator output pulses increases proportionally with Current In. In FIG. 4, digital current integrator output frequency $f_1$ is greater than the frequency $f_0$ of digital current integrator output pulses shown in FIG. 3. Correspondingly, the frequency of production of one-shot pulses of duration $T_s$ increases, thereby decreasing the time interval between one-shot pulses and decreasing the amount of delay time introduced. As a consequence, the frequency of Counter Clock increases and elapsed time counter 60 will reach its prescribed count over a length of time that is reduced in inverse proportion to the increase in beam current.

Figure 5:
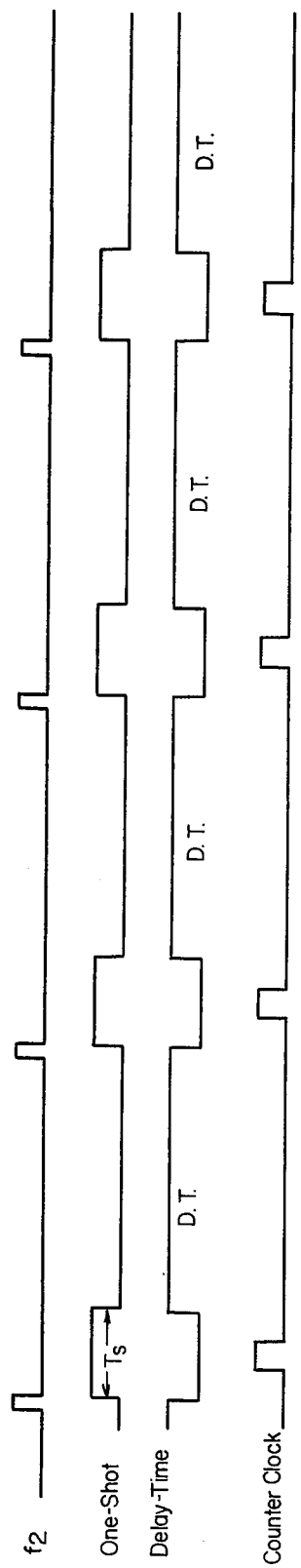

Conversely, if beam current decreases, the digital current integrator output frequency will decrease. FIG. 5 presents a timing diagram wherein digital current integrator output pulse frequency $f_2$ is less than the frequency $f_0$ in the timing diagram of FIG. 3. As a result, one-shot pulses of duration $T_s$ occur less frequently; that is, the pulses are spaced farther apart, and the amount of introduced delay time is increased. Correspondingly, the rate of occurrence of Counter Clock pulses issued from gate 62 decreases, and elapsed time counter 60 counts up to the prescribed count in a longer period of time.

Figure 1:
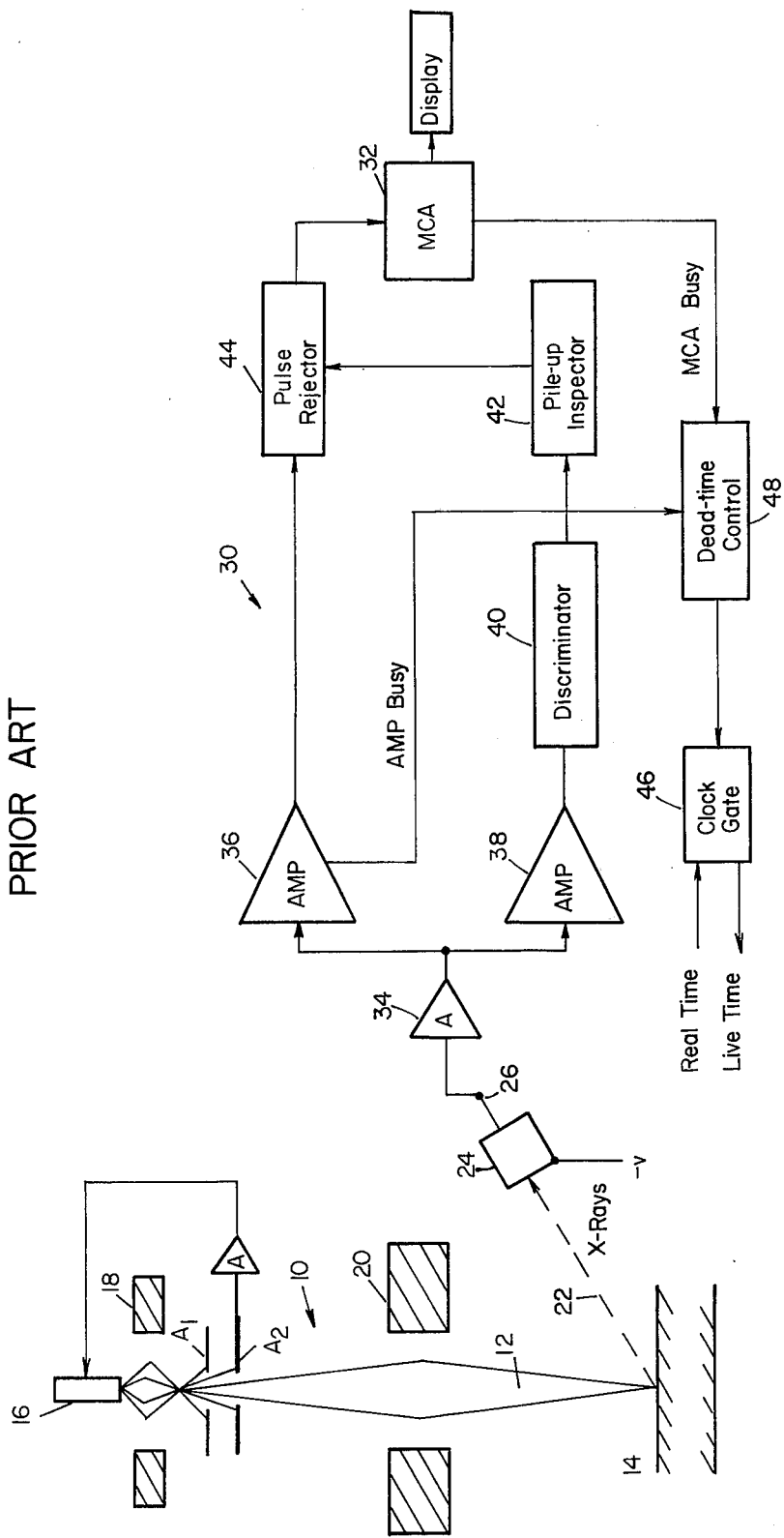
FIG. 1 is a general diagram of a prior art energy dispersive x-ray analysis column instrument.
Figure 6:
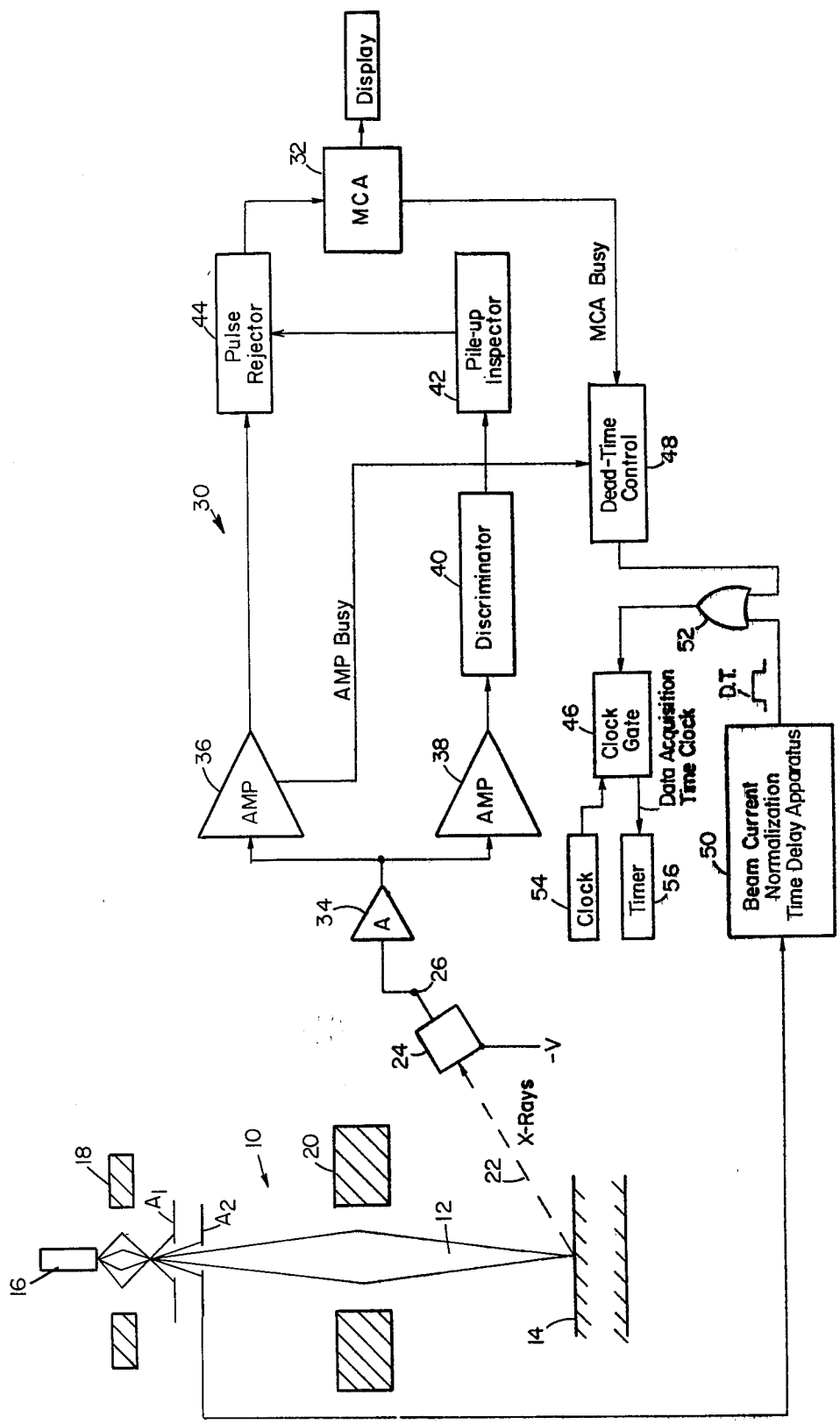
FIG. 6 is a general system diagram of the prior art energy dispersive x-ray analysis column instrument provided with beam current normalization apparatus in accordance with the present invention.

The beam current normalization technique of the present invention may be most advantageously incorporated in prior art electron beam column instruments like that shown in FIG. 1. Referring to FIG. 6, a prior art electron beam column instrument having incorporated therein beam current normalization capability in accordance with the present invention is diagrammed. As shown, a sample of electron flux of electron beam 12 is obtained by aperture plate $A_2$, developing a current, to be referred to as "beam current," proportional to the actual "probe" or "specimen" current present in the focused spot on specimen 14. The beam current obtained at aperture $A_2$ is input to beam current normalization time delay apparatus 50 which develops a Delay Time signal (D.T.) as a function of beam current. The Delay Time signal is combined in OR gate 52 with the normal system dead time signal from dead time control 48. The output of OR gate 52 is applied as the enabling input to clock gate 46 which controls the passage of clock pulses from clock 54 to an elapsed time counter 56. Clock 54 generates the "Real Time" clock indicated in the prior art system shown in FIG. 1. The output of clock gate 46 may be referred to as the "ANALYSIS Time Clock."

As will be recalled from the discussion of the background to the invention, the signal processing circuitry and pulse height analyzer of an electron column instrument require a certain amount of time to perform their associated functions, during which time x-rays emitted from a specimen cannot be counted. This time is referred to as "dead time." The solution developed in the art to overcome the problems created in x-ray intensity count accumulations by the presence of dead time is that of basing data accumulation on the "live-time" of the analyzer. This has been achieved by the use of a "live-time clock" which is derived by controlling the real time clock to govern the x-ray intensity count accumulation time. The use of a controlled, live-time clock on a preset time basis results in an extension of the time required to complete data collection. That is, the actual acquisition time is extended by the amount of system dead time. Thus, the system dead time signal is used in a column instrument to base data accumulations on a fixed amount of analyzer live-time.

Because data accumulation over a defined beam current integral is related to the actual time of data collection, beam current normalization through adjustment of the analysis time period can be readily combined with normal system dead time compensation. An embodiment of this concept is represented by the diagram of FIG. 6, and further expanded upon in the diagram of FIG. 7.

Figure 7:
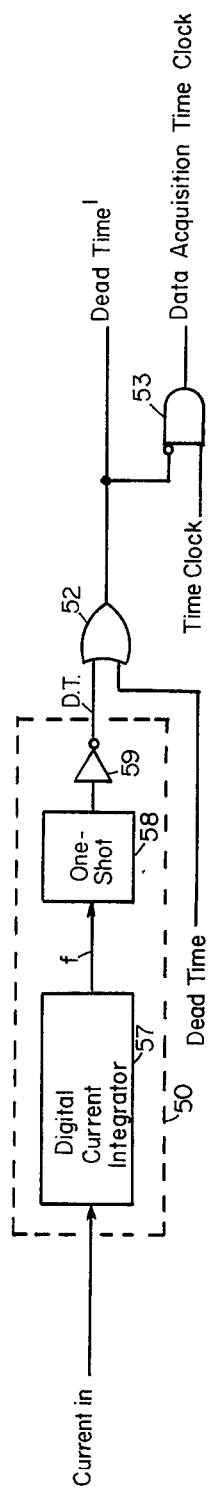
FIG. 7 is a generalized block diagram of the manner of incorporation of beam current normalization in accordance with the present invention in an EDS analyzer having access to the normal EDS analyzer dead time signal.

In FIG. 7, a current proportional to beam current, i.e. Current In, is input to a digital current integrator 57 which produces narrow pulses at a frequency f. The output pulses of digital current integrator 57 are applied to a one-shot 58 producing pulses of a prescribed duration. The output pulses of one-shot 58 are inverted by inverter 59 and output as a Delay Time (D.T.) signal. OR gate 52 receives as inputs both the Delay Time signal from inverter 59 and the normal analyzer dead time signal, and generates in response to those inputs the signal Dead Time'.

Figure 8:
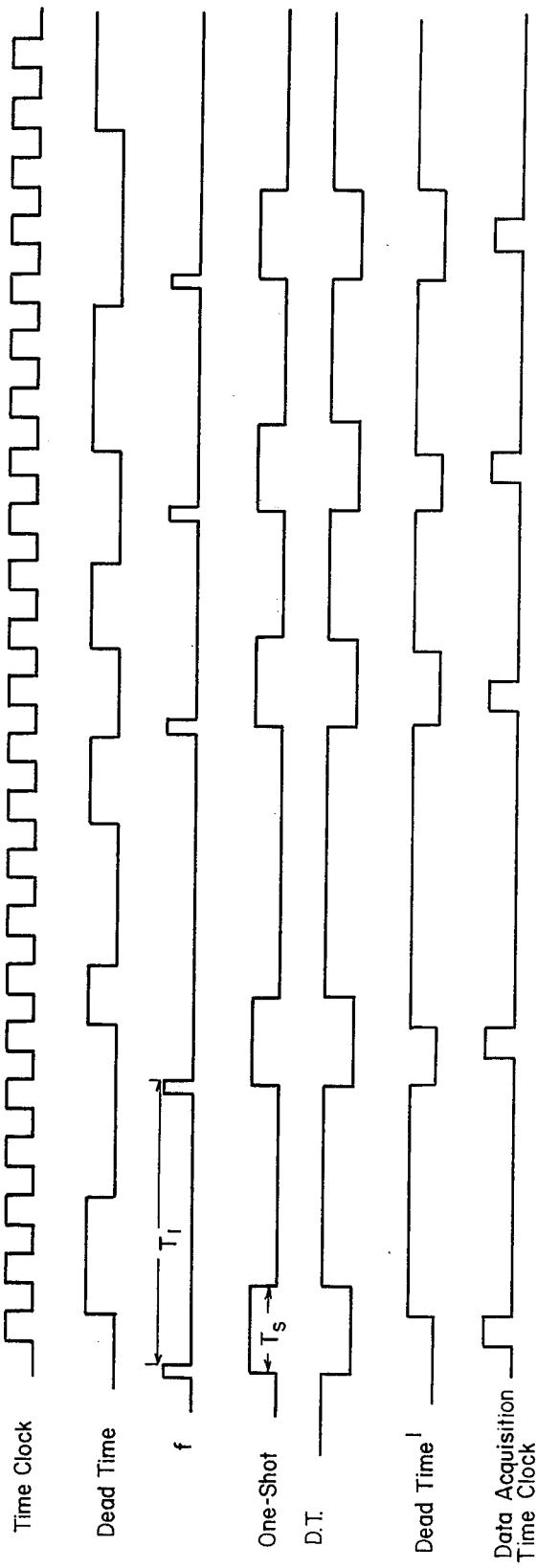
FIG. 8 is a timing diagram illustrating the operation of the diagrammed structure of FIG. 7.

Referring now to the timing diagram of FIG. 8, a system dead time signal normally used to control the time of data acquisition is indicated along with the signal f generated by the digital current integrator. The period of the digital current integrator output pulses is referenced as $T_I$. The one-shot pulses of fixed duration $T_s$ and the Delay Time signal D.T. are indicated also.

Desirably, the one-shot pulse time period $T_s$ is chosen so that for some preset beam current level, the Delay Time signal D.T. will be "high" for a prescribed fractional portion of time $T_I$ and acquisition time. A variation in beam current, producing a variation in the frequency of the digital current integrator output f will effect a change in the Delay Time signal D.T. If the period $T_I$ decreases, representing an increase in frequency, the fractional portion of the time period $T_I$ and data acquisition time during which the signal D.T. is "high" is reduced. Conversely, if the period $T_I$ increases, representing a decrease in frequency, the fractional portion of the time period $T_I$ and data acquisition time that the signal D.T. is "high" increases.

The Dead Time' signal is "high" whenever either the Delay Time signal D.T. or the normal analyzer dead time signal is "high." As indicated in the timing diagram, whenever Dead Time' is "low," clock gate 53 is enabled to permit passage of time clock pulses as Analysis Time Clock pulses. For the indicated dead time and Delay Time signals, a Analysis Clock pulse sequence is shown in the lower trace of FIG. 8.

To further describe the operation, assume an analysis time period of, for example, 100 seconds. Because some of the electron flux strikes the specimen during times that the system is "dead" and unable to count produced x-rays, the "effective" beam current is the fractional live-time of the system. If a count rate and shaping time constant yield a 40% dead time (i.e. 60% live-time), the elapsed data acquisition time period for a dead time compensated column instrument will be 167 seconds. This assumes, however, that the count is not changed as a function of other parameters, such as beam current.

Because the compensating signal dead time is combined with the beam current related Delay Time signal, the "effective" beam current is the product of the fractional live-time of the system and the fractional portion of the integrator pulse period $T_I$ occupied by the one-shot 58 output pulse duration $T_s$. If the frequency of the digital current integrator output pulses is such that for the fixed duration one-shot pulse, delay time is 70% of the integrator pulse time period $T_I$, then the one-shot pulse duration $T_s$ is 30% of the period $T_I$. Consequently, the data acquisition time will be 555.5 seconds (60% live-time × 30% delay time = 18%; 18% of 555.5 = 100), and analysis time will be 333.3 seconds (30% of 333 = 100).

To retain an analysis time of 100 seconds, the effect of delay time must be considered. Since delay time extends analysis time, the preset analysis time should be reduced to an amount that will, upon extension by delay time, result in the desired analysis time. Thus, rather than presetting 100 seconds, a time of 0.3 × 100 = 30 seconds should be set. Thus, analysis time becomes 30/0.3 = 100 seconds and the acquisition time becomes 30/(0.3) (0.6) = 167 seconds.

If beam current remains stable, but the count rate increases as the electron beam scans across a specimen, system dead time will increase, reducing the fractional live-time and further increasing the data acquisition time period. For example, if the count rate yields a 50% dead time (i.e., 50% live-time), the elapsed data acquisition time will become 666.6 seconds rather than 555.5.

If beam current is unstable and drifts from the preset current level, the number of characteristic x-rays produced will vary proportionally. As has been explained, by making x-ray intensity count accumulation on a fixed beam current integral, inaccuracies in the count accumulation due to instability in the beam current can be overcome.

If, for example, beam current decreases by 20%, the frequency of pulses produced from digital current integrator 57 will decrease by 20%, with the period $T_I$ increasing to 1.25 times its original value at the preset current level. To maintain a fixed beam current integral for a 20% decrease in beam current, analysis time must increase to a value that is in inverse proportion to a ratio of the new beam current to the present beam current level. Since a 20% decrease results in a beam current that is 8/10 (0.8) the preset beam current level, analysis time must be extended to 1.25 times the original analysis time. (1/0.8 = 1.25). Therefore, the analysis time needs to be extended from 333.3 seconds to 416.6 seconds, thus extending the data acquisition time to 694.4 seconds.

Because the one-shot pulse duration $T_s$ is fixed, the increased time between digital current integrator pulses, $T_I$ is taken up by delay time. Thus, although the time duration $T_s$ during which the one-shot pulse is "high" remains fixed, the fractional portion of time within the period $T_I$ varies. The fractional portion can be expressed as $T_s/T_I$, or $1-(D.T./T_I)$. Because delay time at the present beam current level was 70%, the period $T_S$ was 30% or 0.3 $T_{I0}$. Thus, the new fractional portion that the period $T_S$ occupies is $T_S/T_{I1}$. Because the new digital current integrator pulse time period, which may be referenced as $T_{I1}$, is 1.25 times the period for the preset beam current, i.e. 1.25 $T_{I0}$, the fractional portion of time during which the Delay Time signal is "low" can be expressed as 0.3 $T_{I0}$/1.25 $T_{I0}$, which reduces to 0.24 or 24%. Assuming that the fractional portion of system live-time is not altered and remains at 60%, the variation in introduced delay time results in an analysis time of 30/(0.24) = 125 seconds a data acquisition time period of 30/(0.24)(0.6) = 208.3 seconds, the required time to provide x-ray intensity count accumulation over a fixed beam current integral.

If the beam current should increase by 20%, the frequency of digital current integrator output pulses will increase proportionately, and the time period $T_I$ between pulses decreases to 1/1.2 $T_{I0}$ or 0.833 $T_{I0}$. The time that Delay Time signal D.T. is "high" is shortened by the same absolute time that the period $T_{I0}$ is shortened. Because the one-shot pulse width $T_s$ is fixed in duration, the fractional portion of time within the period $T_I$ occupied thereby becomes greater, increasing from 30% at the preset beam current level to 36% at the increased beam current level. Accordingly, at a 20% increase in beam current, analysis time would become 30/(0.36) = 83.3 seconds and the data acquisition time period would be reduced to 138.8 seconds, i.e. 30/(0.36)(0.6).

To verify the correctness of the data acquisition time period, consider that to have a fixed beam current integral with a 20% increase in beam current, the acquisition time must be decreased in inverse proportion, i.e. 83.3% of the original analysis time period of 167 seconds, or 138.8 seconds.

The combination of the Delay Time signal and the normal dead time signal to yield a new dead time signal (i.e. Dead Time') may be viewed as the generation of a modulated EDS analyzer dead time signal.

Figure 9:
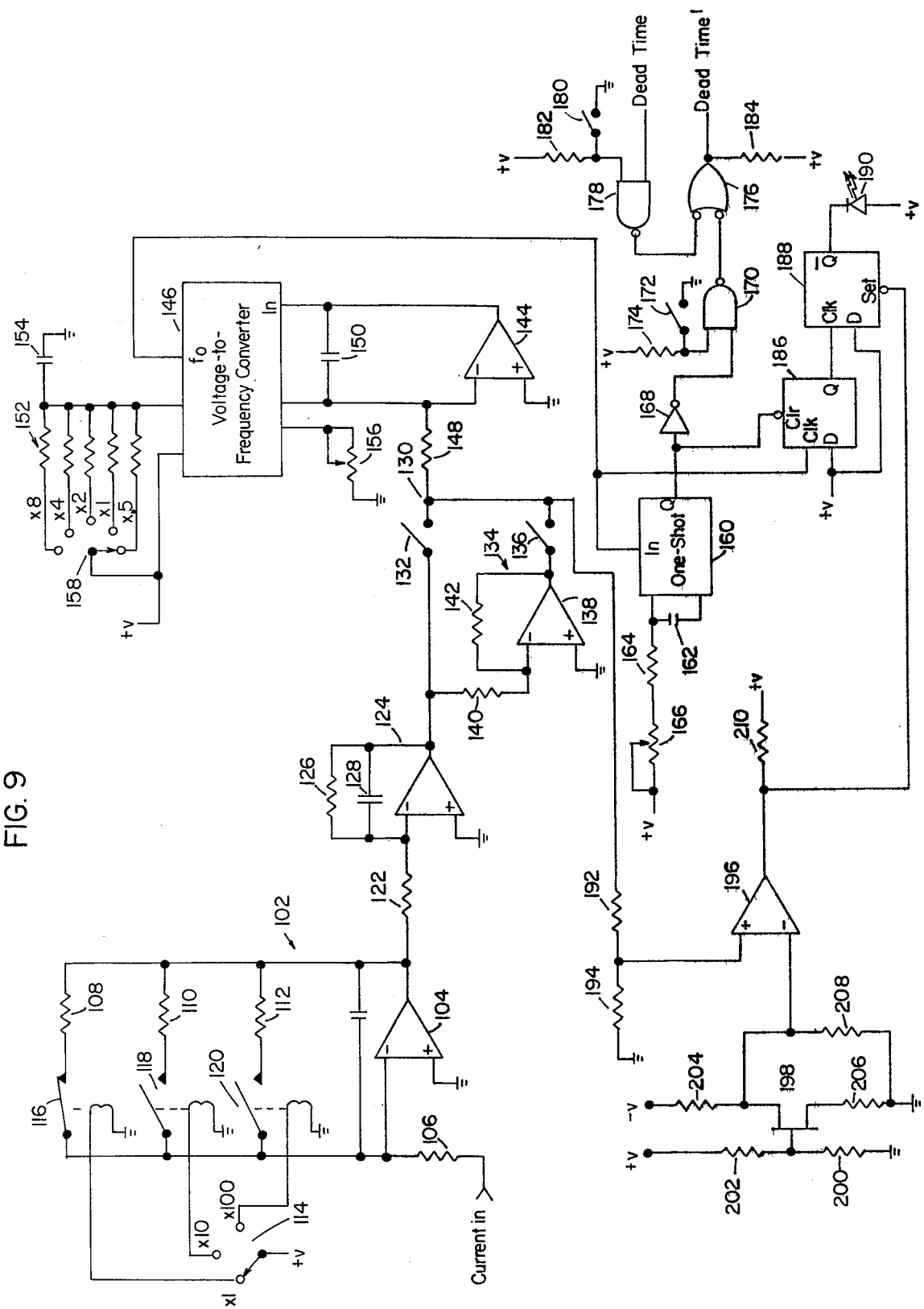
FIG. 9 is a schematic diagram of an illustrative embodiment of the present invention in the context of an arrangement such as that diagrammed in FIG. 7.

Referring now to FIG. 9, there is presented a detailed schematic diagram of one embodiment of circuitry for implementing the functions diagrammed in FIGS. 6 and 7. Current In is applied to an input terminal 100 connected to a current-to-voltage converter generally indicated as 102. The current-to-voltage converter is built around a low bias current operational amplifier 104. An input resistor 106 interconnects input terminal 100 and the inverting input of op-amp 104. The gain of circuit 102 is established by a selected one of feedback resistors 108, 110 and 112. The gain is set by connecting into the feedback loop of op-amp 104 an appropriate one of the feedback resistors. Gain control is provided by gain control switch 114 and relays 116, 118, 120. The resistance magnitude of resistors 108, 110, 112 are scaled in magnitudes of ten, with resistor 108 being of the lowest order of magnitude.

As diagrammed in FIG. 9, the gain control switch 114 is set on a unity gain setting (i.e., X1). As a result, the coil of relay 116 is energized and the contact thereof is closed connecting resistor 108 into the feedback loop of op-amp 104. The gain of circuit 102 is a ratio of the resistance value of the feedback resistor to the resistance value of input resistor 106. Accordingly, if the values of resistors 108 and 106 are the same, a unity gain results. Correspondingly, to obtain gains of 10 and 100, resistors 110 and 112, respectively, are 10 times and 100 times greater in resistance value than resistor 106.

The output of op-amp 104 is applied to input resistor 122 connected to the inverting input of operational amplifier 124. A parallel combination of resistor 126 and capacitor 128 comprises a feedback loop. The output of amplifier 124 can be applied directly to node 130 via switch 132 or routed through inverter circuit 134 and switch 136. Inverter 134 comprises an operational amplifier 138 having input resistor 140 and feedback resistor 142, which are of equal value, providing a unity gain.

A ramp generator circuit 144 for the voltage-to-frequency converter 146 is connected by input resistor 148 to node 130. Ramp generator 144 comprises an operational amplifier integrator having a feedback capacitor 150. The voltage-to-frequency converter 146 is desirably a Raytheon RM4151 device. The combination of ramp generator 144 and device 146 constitutes a precision voltage-to-frequency converter constructed in accordance with the typical applications for RM4151 devices described in part VI of the Raytheon Data Book.

A selected one of resistors in resistor bank 152, capacitor 154, and potentiometer 156 established the functional relationship between the output frequency of converter 146 and the input voltage to ramp generator 144. The pulse width is a function of the selected resistor in resistor bank 152 and capacitor 154. Output frequency range selection is provided by rotary switch 158 which provides for the selection of a desired one of the resistors in resistor bank 152. As indicated, at each position of the switch 158, the output frequency is varied by a factor of two, either doubling the frequency or halving the frequency.

The output of voltage-to-frequency converter 146 is applied to one-shot device 160 which triggers on the negative-going transition of the voltage-to-frequency converter output pulses. One-shot 160 generates a pulse at the Q output of a duration determined in accordance with the values of capacitor 162 and resistor 164, and the setting of potentiometer 166. One-shot 160 may desirably be a SN74LS122 retriggerable monostable multivibrator manufactured by Texas Instruments, Inc.

The output of one-shot 160 is inverted by inverter 168 and applied as an input to NAND gate 170. The second input to gate 170 is selected by the setting of a delay time switch 172 which either grounds the input of gate 170 to establish a logic "0" or permits the input to be pulled "high" through resistor 174.

The output of NAND gate 170 is applied as an input to "negative—true input" OR gate 176 having as a second input thereto the output of NAND gate 178. NAND gate 178 receives as one input the normal analyzer dead time signal from dead time control 48 shown in FIG. 6. The second input to NAND gate 178 is controlled by dead time switch 180 which either grounds the gate input to establish a logic "0" or permits the input to be pulled "high" through resistor 180. The output of OR gate 176 is connected to a pull-up resistor 184 and provides the Dead Time' signal.

The output of voltage-to-frequency converter 146 is also applied as a clock input to D-type flip-flop 186, which has the D input tied "high." The clear input to flip-flop 186 is obtained from the Q output one-shot 160. The Q output of flip-flop 186 is applied as a clock input to D-type flip-flop 188 which also has its D input tied "high." The $\overline{Q}$ output of flip-flop 188 is connected to the annode of a light emitting diode 190.

The signal applied to node 130 is also applied to a voltage divider network comprising equal value resistors 192 and 194. The divider output, providing one-half the voltage on node 130, is applied to the non-inverting input of operational amplifier 196, which is connected as a comparator. The inverting input of op-amp 196 is connected to a negative reference voltage source comprising a field effect transistor 198, bias resistors 200 and 202, resistors 204 and 206, and load resistor 208. The output of op-amp 196 is connected to a pull-up resistor 210 and to the Set input of flip-flop 188. The comparator compares half of the voltage at node 130 to the negative reference potential. If the voltage at node 130 is more negative than the reference potential, the comparator output goes "low," setting flip-flop 188 and turning on LED 190.

Pulses from voltage-to-frequency converter 146 trigger one-shot 160, producing a pulse of fixed width. Because of the inversion of the one-shot output by inverter 168, gate 170 has a logic "one" applied thereto from inverter 168 only during the time period between one-shot pulses. When delay time switch 172 is open, gate 170 is enabled and one-shot pulses are passed through to OR gate 176. If dead time switch 180 is open, dead time pulses from the analyzer dead time control are inverted by gate 178 and combined with the one-shot pulses to generate Dead Time'.

If delay time switch 172 is closed, gate 170 is disabled and Dead Time' is the same as the dead time input from the analyzer dead time control. If dead time switch 180 is closed, gate 178 is disabled and Dead Time' becomes only the beam current related Delay Time signal.

The output pulses of the voltage-to-frequency converter 146 clock flip-flop 186 to produce a "set" condition on the Q output thereof. The one-shot output clears flip-flop 186. One-shot 160 triggers a "high" pulse on a "high-to-low" transition, while flip-flop 186, on the other hand, is a rising edge triggered device. Accordingly, flip-flop 186 will be clocked just prior to the triggering of one-shot 160. But, because the Q output of one-shot 160 is applied to the clear input to flip-flop 186, there is no change of state by flip-flop 186. However, if Current In is sufficiently high to produce output pulses from voltage-to-frequency converter 146 that are spaced closely enough together that a clock pulse is applied to flip-flop 186 while the one-shot output pulse is in progress, flip-flop 186 will be clocked to a "set" condition, which further clocks flip-flop 188 to a "set" condition and turns on LED 190. This indicates a current over range condition. It can be appreciated that the point at which a current over range condition will be indicated is a matter of choosing a maximum permissible beam current, with the fixed width of one-shot pulses being established in accordance with that maximum beam current and the relationship between Current In and voltage-to-frequency converter output frequency.

From the foregoing description, it should now be understood that the present invention provides for the accumulation of x-ray intensity counts by an electron beam column instrument, with the count accumulation being normalized to a prescribed beam current by maintaining a fixed beam current integral regardless of beam current instability. Furthermore, by combining the normal system dead time with a beam current dependent delay time signal derived from a digital current integrator, beam current normalization can conveniently be provided in a dead time corrected electron beam column instrument.

To test the performance of the beam current normalization technique of the present invention, test data were collected on two different SEM's, monitoring aperture current on the first and monitoring specimen current on the second SEM. Because the total number of x-rays generated in a specimen is directly proportional to the number of absorbed electrons, the total integral of the x-ray spectrum was used to indicate the absorbed current.

Figure 10A:
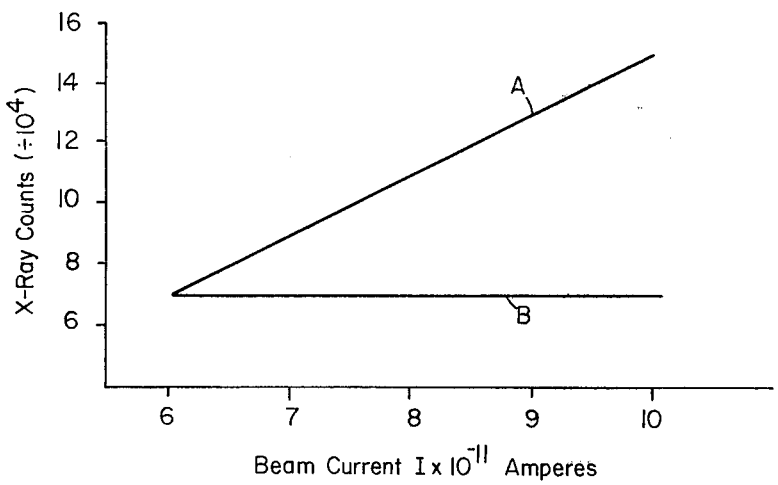
FIG. 10A is a presentation of the results of measurements, in terms of total x-ray counts plotted as a function of aperture current, obtained with and without the present invention.

Referring now to FIG. 10A, there is a graph of total x-ray counts as a function of aperture current. Trace A is a plot obtained without use of the beam current normalization technique of the present invention to compensate column instrument data accumulations. Plot B represents column instrument data accumulation using the beam current normalization technique of the present invention. As indicated, without beam current normalization, the change in x-ray count is linearly proportional to a change in beam current. However, using the beam current compensation technique of the present invention provides an x-ray count which remains constant though beam current varies.

Figure 10B:
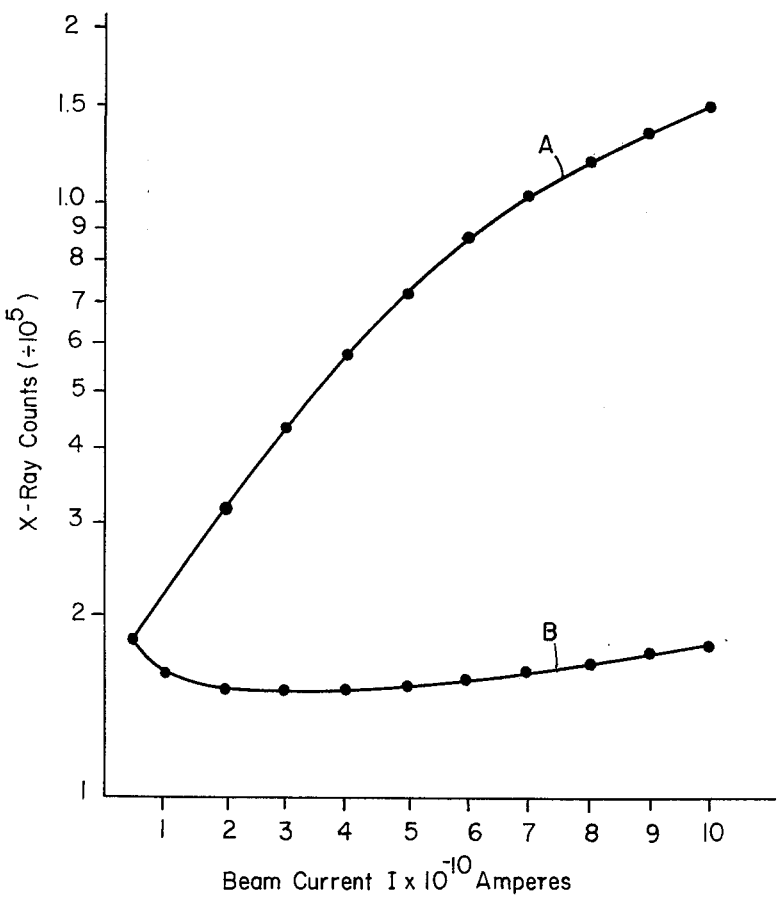
FIG. 10B is a presentation of the results of measurements, in terms of total x-ray counts plotted as a function of specimen current, obtained with and without the present invention.

FIG. 10B presents a plot of total x-ray counts as a function of specimen current. The vertical axis is a log scale. Trace A represents an accumulation of counts without beam current normalization in accordance with the present invention. Trace B represents a count accumulation with beam current normalization in accordance with the present invention. Trace B shows only a 15% variation in count accumulation over the beam current range. The use of data obtained by monitoring the specimen current for quantitative analysis is complicated by the fact that the absorbed current depends upon the average atomic number of the specimen. Since most matrix correction procedures require data that is normalized to fixed incident current (not absorbed current) data normalized to specimen current must be corrected to the proper incident current values before processing.

The foregoing description of the invention has been directed to illustrative embodiments of the present invention for purposes of explanation and illustration. It will be appreciated by those having ordinary skill in the art that the present invention admits to embodiment in many equivalent forms without departing from the teachings of the invention.

For example, it can be understood that the "delay time" signal, rather than being implemented as a signal of varying duration as herein described, could equivalently be implemented as a series of discrete fixed-width pulses of varying number such that the time of actual data accumulation again varies in inverse proportion to variations of beam current.

It can also be understood that in addition to its application to electron column instruments, the invention as herein described is equally applicable to systems for X-ray analysis by other means of excitation, including excitation by charged particle beams and by photons; in such equivalent incorporations, the beam-current monitoring device might be a particle detector, an ionization chamber, or any other sensing device whose output signal is proportional to the intensity of the exciting beam.

What is claimed is:

1. In an electron column instrument for quantitative energy dispersive x-ray microanalysis including an optical system for establishing a focused electron beam of a preset beam current level directed onto an analysis specimen, means for analyzing the spectrum of x-rays emitted from the specimen to accumulate a count of x-ray intensities, and an elapsed time counter for timing out an analysis time period, the improvement comprising:

a beam current sensor for monitoring electron beam current stability; and means for introducing delay time in the elapsed time counting of the analysis time period as a function of electron beam current stability to control the time of actual data accumulation such that x-ray spectral data is acquired over a defined beam current integral.

2. The improvement of claim 1 wherein:

the delay time introducing means introduces delay time in periodically occurring intervals of constant duration so long as beam current remains stable at the preset beam current level and introduces delay time in intervals that differ in duration from the periodic intervals such that the time of actual data accumulation varies in inverse proportion to variations of the beam current from the preset beam current level.

3. The improvement of claim 1 wherein:

the delay time introducing means introduces delay time in intervals of time such that analysis time is varied in inverse proportion to variations of the beam current.

4. The improvement of claim 1 wherein the delay time introducing means comprises:

means for inhibiting operation of the elapsed time counter; and means for actuating the inhibiting means to inhibit elapsed time counting for an interval of time, and means responsive to the stability of electron beam current for controlling the actuating means to produce inhibiting of elapsed time counting in intervals that vary in duration as a function of beam current variations.

5. The improvement of claim 4 wherein:

the actuating means is a retriggerable one-shot circuit; and the control means is a current-to-frequency converter.

6. The improvement of claim 1 wherein:

the delay time introducing means comprises means for introducing delay time in an amount that varies in an inverse proportion to a variation in beam current.

7. In an electron beam column instrument for quantitative energy dispersive x-ray microanalysis including an optical system for establishing a focused electron beam flux of a preset probe current level directed onto an analysis specimen, means for analyzing the spectrum of x-rays emitted from the specimen to accumulate a count of x-ray intensities, an oscillator producing clock pulses, an elapsed time counter receiving clock pulses for timing out an analysis time period, the improvement comprising:

means for monitoring electron beam current stability;

means for inhibiting the counting of clock pulses by the elapsed time counter, the count inhibiting means being responsive to an actuating signal pulse to inhibit counting for an interval of time that corresponds to the duration of the actuating signal pulse;

a pulse generator for generating a signal pulse of a preselected duration in response to a trigger pulse input thereto;

means for producing an actuating signal pulse between pulse generator signal pulses; and a current-to-frequency converter for generating pulses to trigger the pulse generator, the converter generating trigger pulses at a frequency that varies in direct proportion to beam current variations.

8. The improvement of claim 7 wherein the electron beam current stability monitoring means comprises:

an aperture plate disposed in the optical system for stopping an annular section of the electron beam flux to collect a charge thereon; and means responsive to the charge collected by the aperture plate for developing a current proportional to probe current.

9. Apparatus for providing beam current normalization in an EDS analyzer having an elapsed analysis time counter, which comprises:

means for producing a current proportional to beam current;

a digital current integrator producing pulses, each representing the integration of a defined amount of charge, the time interval between pulses being inversely proportional to the current from the current producing means;

a one-shot connected to the digital current integrator for producing a pulse of prescribed duration in response to each pulse from the digital current integrator; and means connected to the one-shot for producing a delay time signal between the prescribed duration pulses to inhibit the elapsed time counter of the EDS analyzer.

10. The apparatus of claim 9 wherein the digital current integrator is a current-to-frequency converter.

11. Apparatus for providing beam current normalization in an EDS analyzer having a dead time control section producing a dead time signal and a timer responsive to the dead time signal for establishing the length of an analysis time period, which comprises:

an electron beam current sensor for providing a current signal proportional to electron beam current;

a digital current integrator connected to the beam current sensor for producing an output pulse waveform signal; and means coupled to the digital current integrator for modulating the analyzer dead time signal in response to the integrator output signal to correct for variations in electron beam current during EDS analyzer data acquisition.

12. The apparatus of claim 11 wherein:
the digital current integrator comprises a current-to-frequency converter.

13. In an electron column instrument for quantitative energy dispersive x-ray microanalysis which includes an optical system for establishing a focused electron beam of a preset beam current level directed onto an analysis specimen, a solid state detector for detecting x-rays emitted from the analysis specimen, signal processing circuitry coupled to the solid state detector for producing a voltage pulse representative of detected x-rays, a pulse height analyzer for analyzing the spectrum of x-rays detected and accumulating a count of x-ray intensities, an elapsed time counter for timing out an analysis time period, an oscillator generating clock pulses to drive the counter, a clock gate coupling the oscillator to the counter for inhibiting or allowing the passage of clock pulses to the counter, and a dead time control circuit for generating a signal indicative of the time period the signal processing circuitry and the analyzer require to process and analyze a detected x-ray, the improvement comprising:

a beam current sensor for providing a current proportional to electron beam current;

a digital current integrator coupled to the beam current sensor for producing an output signal comprising pulses representative of the integration of a fixed amount of charge, the average spacing in time between integrator pulses being inversely proportional to beam current; and logic circuitry operably connected to the digital current integrator and to the dead time control circuit for combining the dead time signal and the integrator output signal and producing a clock gate control signal.

14. The improvement of claim 13 wherein the logic circuitry comprises an OR logic circuit.

15. The improvement of claim 13 wherein the logic circuitry comprises:

a one-shot connected to the digital current integrator for producing a pulse of prescribed duration in response to each integrator pulse;

means connected to the one-shot for providing a delay time signal between the one-shot pulses; and an OR gate connected to the dead time control circuit and to the delay time signal producing means for producing an active output signal condition in response to the delay time signal or to the dead time signal; and means for coupling the OR gate to the clock gate to inhibit elapsed time counting of the analysis time period as a function of electron beam current and instrument dead time such that x-ray spectral data is acquired over a defined beam current integral and dead time correction is provided.

* * * * *

UNITED STATES PATENT OFFICE
CERTIFICATE OF CORRECTION

Patent No. 4,288,692  Dated September 8, 1981

Inventor(s) FREDERICK H. SCHAMBER and JON J. MCCARTHY

It is certified that error appears in the above-identified patent and that said Letters Patent are hereby corrected as shown below:

(Col. 4, Line 45), "bush" should read -- busy --.
(Col. 5, Line 32), "computer" should read -- computed --.
(Col. 1, Line 38), "valve" should read -- value --.
(Col. 1, Line 42), insert -- and -- between "binding" and "are".
(Col. 3, Line 22), "valve" should read -- value --.
(Col. 12, Line 3), insert a comma after "seconds".
(Col. 13, Line 59), "annode" should read -- anode --.

Signed and Sealed this

Eighth Day of December 1981

[SEAL]

Attest:

GERALD J. MOSSINGHOFF

Attesting Officer  Commissioner of Patents and Trademarks